United States Patent
Kamat et al.

(10) Patent No.: US 8,273,918 B2
(45) Date of Patent: Sep. 25, 2012

(54) PROCESS FOR PREPARING TAMSULOSIN HYDROCHLORIDE

(75) Inventors: Anand Gopalkrishna Kamat, Hyderabad (IN); Narsimha Reddy Penthala, Hyderabad (IN); Sivakumaran Meenakshisunderam, Hyderabad (IN)

(73) Assignee: Avrobindo Pharma Ltd., Hyderabad (IN)

( * ) Notice: Subject to any disclaimer, the term of this patent is extended or adjusted under 35 U.S.C. 154(b) by 1149 days.

(21) Appl. No.: 11/991,662

(22) PCT Filed: Aug. 10, 2006

(86) PCT No.: PCT/IB2006/002260
§ 371 (c)(1), (2), (4) Date: Mar. 7, 2008

(87) PCT Pub. No.: WO2007/031823
PCT Pub. Date: Mar. 22, 2007

(65) Prior Publication Data
US 2010/0267987 A1 Oct. 21, 2010

(30) Foreign Application Priority Data
Sep. 12, 2005 (IN) .............. 1270/CHE/2005

(51) Int. Cl.
C07C 303/38 (2006.01)
(52) U.S. Cl. .................. 564/86; 514/603
(58) Field of Classification Search .......... 564/86; 514/603
See application file for complete search history.

(56) References Cited

U.S. PATENT DOCUMENTS

| 4,703,063 | A | 10/1987 | Imai et al. |
| 2006/0036113 | A1 | 2/2006 | Xie |

FOREIGN PATENT DOCUMENTS

| CA | 1282077 | | 3/1991 |
| EP | 0380144 B1 | | 1/1994 |
| WO | WO 02/068382 A1 | | 9/2002 |
| WO | WO 2004/087623 | * | 3/2003 |
| WO | WO 2003/035608 | * | 5/2003 |
| WO | WO 2004/016582 | | 2/2004 |
| WO | WO 2004/022532 A1 | | 3/2004 |
| WO | WO 2005/063702 | * | 7/2005 |

* cited by examiner

Primary Examiner — Peter G O Sullivan
(74) Attorney, Agent, or Firm — Jay R Akhave

(57) ABSTRACT

The invention relates to an process for preparing Tamsulosin hydrochloride of Formula (I) which comprises (i) reacting (R)-(−)-5-(2-amino-propyl)-2-methoxybenzenesulfonamide of Formula (II) with substituted phenoxy compound of Formula (III), wherein Z represents a removing group, such as —$OSO_2CH_3$, —$OSO_2C_6H_4CH_3$, —F, —Br, —Cl, or —I, in a solvent in the presence of an alkaline earth metal oxide to obtain Tamsulosin base and (ii) converting Tamsulosin base into hydrochloride salt in a solvent by addition of aqueous hydrochloric acid.

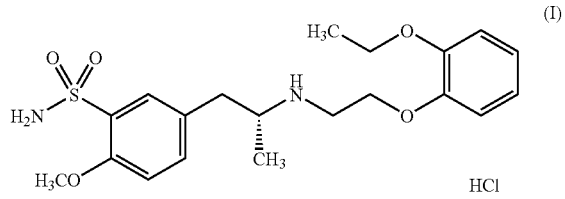

7 Claims, No Drawings

PROCESS FOR PREPARING TAMSULOSIN HYDROCHLORIDE

FIELD OF THE INVENTION

The invention relates to an improved process for preparing the (R)-(−)-5-[2-[[2-(2-ethoxyphenoxy)ethyl]amino]propyl]-2-methoxybenzenesulfonamide monohydrochloride of Formula I.

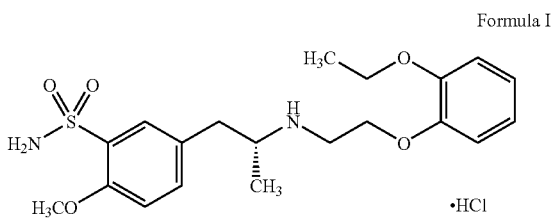

Formula I

BACKGROUND OF THE INVENTION (R)-(−)-5-[2-[[2-(2-ethoxyphenoxy)ethyl]amino]propyl]-2-methoxybenzenesulfonamide is known as Tamsulosin. Presently Tamsulosin is being marketed as its hydrochloride salt under the Trade name FLOMAX. It is an α-adrenergic antagonist used preferably for treating benign prostatic hyperplasia.

U.S. Pat. No. 4,703,063 describes two processes for the preparation of Tamsulosin, one of which involves the conversion of a hydroxy substituted analogue of Tamsulosin, i.e., a compound having the Tamsulosin structure but contains a hydroxyl substituent at a position α to the benzenesulfonamide ring, by halogenation followed by reduction and the other involves condensation of an appropriately substituted benzyl methyl ketone with the substituted phenoxy amine, followed by reduction of the resulting imino compound.

The above described processes are non-stereospecific and the final product requires an additional step of resolution of enantiomers to specifically obtain (R)-enantiomer tamsulosin.

CA 1,282,077 discloses a process to prepare Tamsulosin wherein (R)-enantiomer of sulfonamide amine has been condensed with ethoxy phenoxy bromide in dimethylformamide to obtain Tamsulosin (Scheme I), which was purified by crystallization before converting into hydrochloride salt.

Scheme I

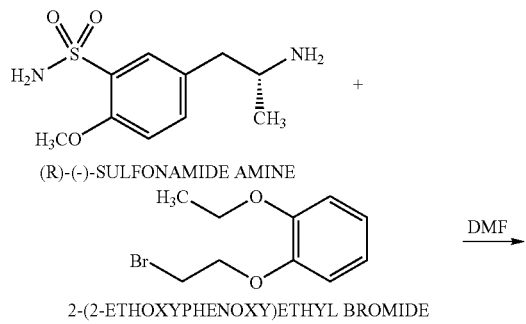

(R)-(-)-SULFONAMIDE AMINE 2-(2-ETHOXYPHENOXY)ETHYL BROMIDE

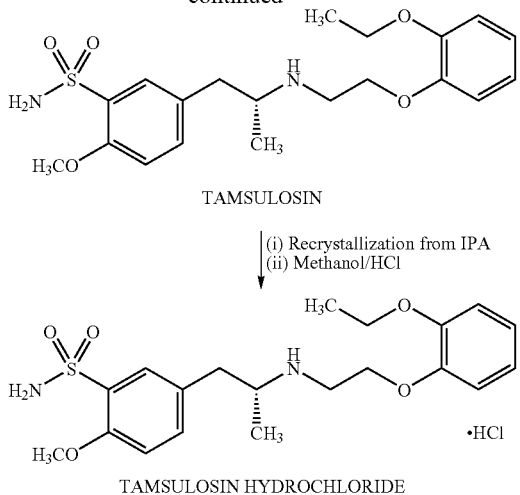

TAMSULOSIN (i) Recrystallization from IPA
(ii) Methanol/HCl

TAMSULOSIN HYDROCHLORIDE

As per the above described process, Tamsulosin hydrochloride is obtained in low yield, and therefore this process is not suitable for commercial production.

WO 2002/068382 A1 discloses a process to prepare sulfamoyl substituted phenethylamine derivatives including Tamsulosin. The described process involves a coupling reaction between (R)-(−)-5-(2-aminopropyl)-2-methoxybenzenesulfonamide with an acid or a corresponding acid chloride or mixed anhydride to produce Tamsulosin amide and thereafter reduction of the obtained compound gives Tamsulosin. This coupling reaction presents the disadvantage that the acid or acid chloride or anhydride should be provided in a high purity in order to obtain a good yield in the coupling reaction; and it is known in the art that purification of such products is not always easy.

WO 2004/022532 A1 discloses a process to prepare Tamsulosin (Scheme II) wherein protected amine is used during condensation with ethoxy phenoxy derivative to obtain protected Tamsulosin. In this process, an additional step of removing the protecting group to obtain Tamsulosin is involved.

Scheme II

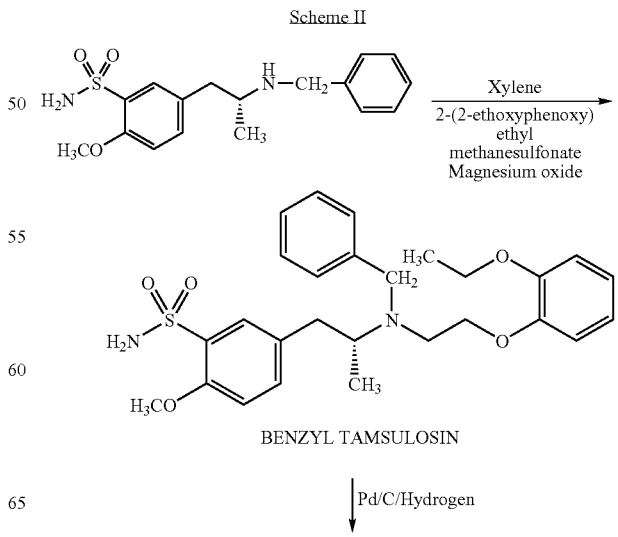

BENZYL TAMSULOSIN

Pd/C/Hydrogen

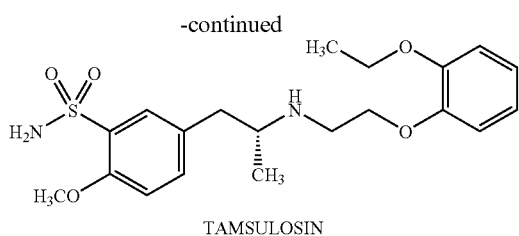

TAMSULOSIN

This process involves the use of a protected amine derivative, which needs to be deprotected after the formation of Tamsulosin.

EP 0 380 144 B1 describes a process for preparing Tamsulosin and the like, in stereospecific form, by reaction of a benzenesulfonamide amine with predetermined stereospecificity, with 2-(2-ethoxyphenoxy)ethyl halide, specifically the bromide. In this process, Tamsulosin base has been purified with column chromatography.

WO 2004/016582 discloses a process to prepare Tamsulosin hydrochloride (Scheme III). This process involves two additional steps, first the protection of amine group before condensing with ethoxy phenoxy halide and thereafter the deprotection to obtain Tamsulosin. In all the examples given in this application, column chromatography has been used to purify Tamsulosin base before converting into hydrochloride salt.

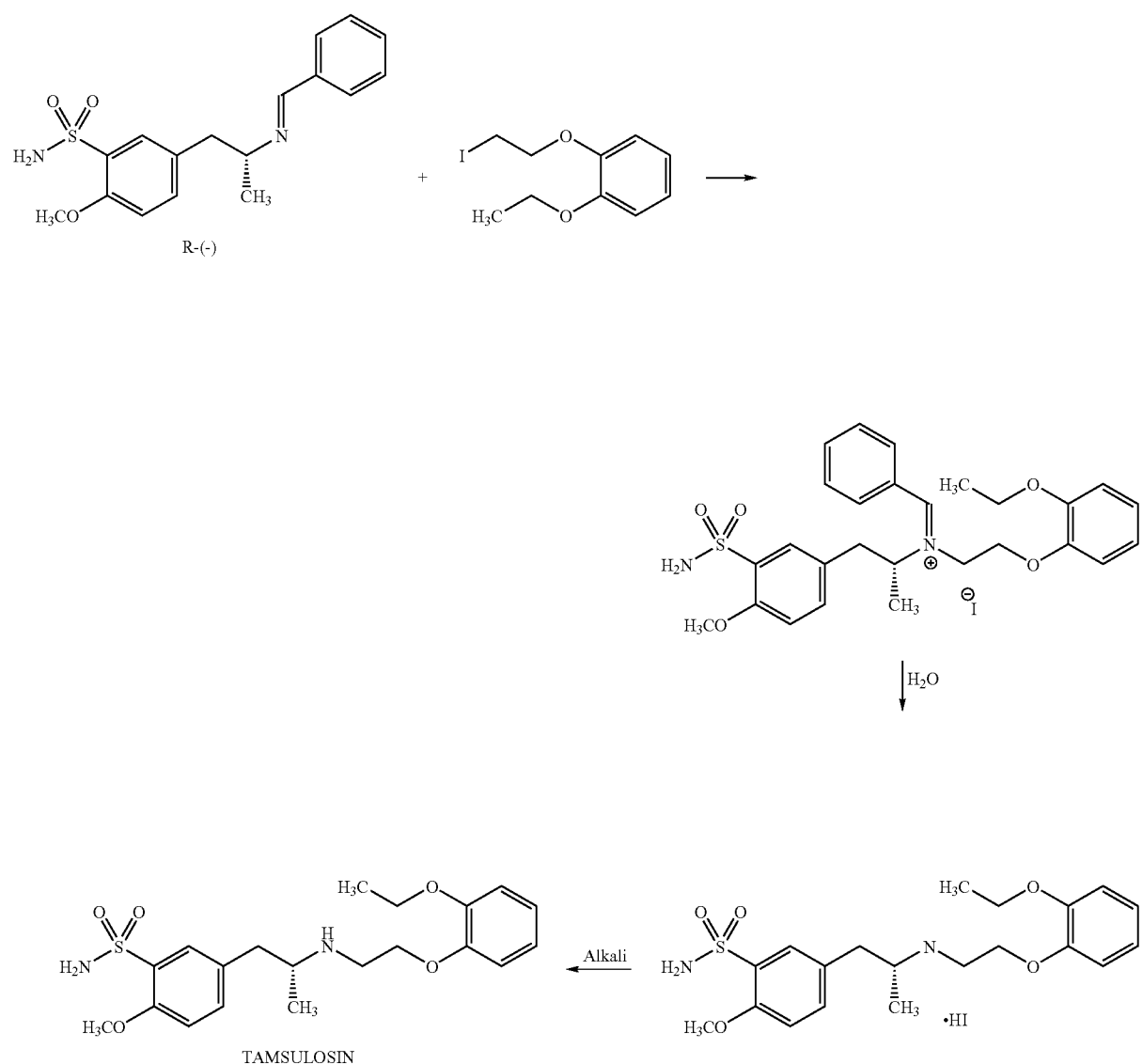

Scheme III

In view of the above difficulties, the instant invention describes a new economical and industrially advantageous method to prepare Tamsulosin by using alkaline earth metal oxides as acid neutralizing agent in the alkylation reaction.

OBJECTIVE

The objective of the present invention is to provide an improved process for preparing highly pure Tamsulosin hydrochloride in high yield.

Yet another objective of the present invention is to provide a simple, industrially advantageous process to manufacture Tamsulosin hydrochloride.

SUMMARY OF THE INVENTION

The present invention relates to an improved process to prepare Tamsulosin hydrochloride of Formula I

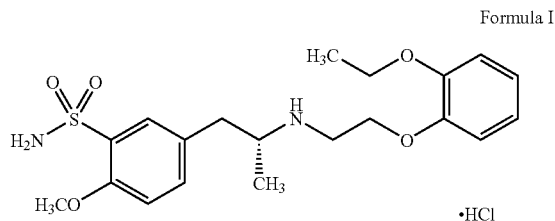

Formula I

·HCl which comprises
(i) reacting (R)-(−)-5-(2-aminopropyl)-2-methoxybenzenesulfonamide of Formula II

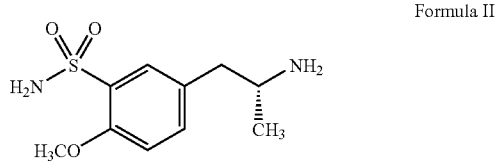

Formula II with substituted phenoxy compound of Formula III,

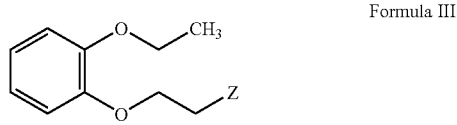

Formula III wherein Z represents a removing group such as, —$OSO_2CH_3$, —$OSO_2C_6H_4CH_3$, —F, —Br, —Cl, or —I, in a solvent in the presence of an alkaline earth metal oxide to obtain Tamsulosin base and
(ii) converting Tamsulosin base into hydrochloride salt in a solvent by addition of aqueous hydrochloric acid.

DETAILED DESCRIPTION OF THE INVENTION

Specifically, the present invention involves reacting compound of Formula II with compound of Formula III in presence of an alkaline earth metal oxide selected from calcium oxide, barium oxide, magnesium oxide and the like. The said alkylation reaction is accomplished in presence of a solvent selected from $C_{1-4}$ alcohol such as methanol, ethanol, isopropanol, isobutyl alcohol and mixtures thereof, and preferably isobutyl alcohol. Typically the alkylation reaction is completed by heating under reflux at 60-100° C. and preferably at 80-90° C.

The major advantage realized in the present process is the use of alkaline earth metal oxide, an acid neutralizing agent, to promote the alkylation reaction. Alkaline earth metal salts are insoluble in the reaction medium and are removed easily by filtration after the alkylation reaction is over.

In yet another embodiment of the present invention, the solvent employed during formation of Tamsulosin hydrochloride and during its purification is selected from $C_{1-4}$ alcohol such as methanol, ethanol, isopropanol, isobutyl alcohol and mixtures thereof, and preferably methanol.

The invention is illustrated with the following examples, which are provided by way of illustration only and should not be construed to limit the scope of the invention.

Example 1

Step (i)

Preparation of Crude Tamsulosin Hydrochloride

A mixture of (R)-(−)-5-(2-aminopropyl)-2-methoxybenzenesulfonamide (20 g, 0.082 mol), 2-(2-ethoxyphenoxy) ethyl methanesulfonate (19.18 g, 0.074 mol), calcium oxide (4.6 g, 0.821 mol) and isobutyl alcohol (300 ml) was heated at 80-85° C. for 25 h. The reaction mass was filtered to remove calcium salts and the residue was washed with hot isobutyl alcohol (2×10 ml, 70° C.). Thereafter, pH of the filtrate was adjusted to 1.0 using hydrochloric acid (10 g) at 60-65° C. and the resulting product slurry was allowed to cool to 0-5° C. The solid thus obtained was filtered, washed with precooled isobutyl alcohol (2×10 ml, 5° C.). Yield: 43 g (wet).

Step (ii)

Preparation of Pure Tamsulosin Hydrochloride (R)-(−)-5-[2-[[2-(2-ethoxyphenoxy)ethyl]amino]propyl]-2-methoxybenzenesulfonamide hydrochloride (43 g, wet) was suspended in methanol (140 ml) and stirred at 55-60° C. for 30 min. This suspension was cooled to 0-5° C., filtered and washed with precooled methanol (10 ml, 0° C.). The filtered product (23 g) was dissolved in methanol (400 ml) at 55-60° C. and treated with carbon (0.6 g) at the same temperature. Carbon was removed through hyflo and the residue was washed with hot methanol (2×25 ml, 60° C.). The filtrate was concentrated under vacuum to a volume of about 150 ml. The product slurry was cooled and stirred at 0-5° C. for 2 h. The mass was filtered, washed with precooled methanol (10 ml, 0° C.) and dried to obtain Tamsulosin hydrochloride. Yield: 19 g. Chromatographic Purity: 99.76% (HPLC).

Example 2

Step (i)

Preparation of Crude Tamsulosin Hydrochloride

A mixture of (R)-(−)-5-(2-aminopropyl)-2-methoxybenzenesulfonamide (3 g, 0.0123 mol), 2-(2-ethoxyphenoxy) ethyl methanesulfonate (2.88 g, 0.011 mol), calcium oxide (0.52 g, 0.0093 mol) and ethanol (60 ml) was heated at 78-80° C. for 35 h. The reaction mass was filtered and the residue was washed with hot ethanol (4 ml, 70° C.). The pH of filtrate was adjusted to 1.0 using hydrochloric acid (1.68 g) at 60-65° C. and the resulting product slurry was allowed to cool to 0-5° C.

The solid thus obtained was filtered, washed with precooled ethanol (4 ml, 5° C.). Yield: 6 g (wet)

Step (ii)

Preparation of Pure Tamsulosin Hydrochloride (R)-(−)-5-[2-[[2-(2-ethoxyphenoxy)ethyl]amino]propyl]-2-methoxybenzenesulfonamide hydrochloride (6 g, wet) was suspended in methanol (21 ml) and stirred at 55-60° C. for 30 min. The suspension was cooled to 0-5° C., filtered and washed with precooled methanol (4 ml, 0° C.). The filtered product (3.1 g) was dissolved in methanol (60 ml) at 55-60° C. and treated with carbon (0.1 g) for 15 min. Carbon was removed by filtration and the filtrate was concentrated under vacuum to a volume of about 25 ml. The slurry was cooled and stirred at 0-5° C. for 2 h. The product was filtered, washed with precooled methanol (4 ml, 0° C.) and dried to obtain Tamsulosin hydrochloride. Yield: 2.65 g. Chromatographic Purity: 99.70% (HPLC).

Example 3

Step (i)

Preparation of Crude Tamsulosin Hydrochloride

A mixture of (R)-(−)-(2-aminopropyl)-2-methoxybenzenesulfonamide (3 g, 0.0123 mol), 2-(2-ethoxyphenoxy)ethyl bromide (3.05 g, 0.0124 mol), calcium oxide (0.52 g, 0.0093 mol) and isobutyl alcohol (45 ml) was heated at 80-90° C. for 22 h. The reaction mass was filtered and the residue was washed with hot isobutyl alcohol (4 ml, 70° C.). The pH of filtrate was adjusted to 1.0 with hydrochloric acid at 60-65° C. and the contents were cooled to 0-5° C. The solid thus obtained was filtered, washed with precooled isobutyl alcohol (4 ml, 5° C.). Yield: 7.5 g (wet)

Step (ii)

Preparation of Pure Tamsulosin Hydrochloride (R)-(−)-5-[2-[[2-(2-ethoxyphenoxy)ethyl]amino]propyl]-2-methoxybenzenesulfonamide hydrochloride (7.5 g) was suspended in methanol (20 ml) and stirred at 55-60° C. for 30 min. The suspension was cooled to 0-5° C. and filtered. The product (3.5 g), thus obtained, was dissolved in methanol (60 ml) at 55-60° C. and treated with carbon (0.1 g). Thereafter, carbon was removed through hyflo and the filtrate was concentrated to a volume of about 25 ml under vacuum. The product slurry was cooled to 0-5° C. The product was collected by filtration, washed with precooled methanol (4 ml, 0° C.) and dried to obtain Tamsulosin hydrochloride. Yield: 2.45 g. Chromatographic Purity: 99.89% (HPLC).

We claim:

1. An improved process to prepare Tamsulosin hydrochloride of Formula I

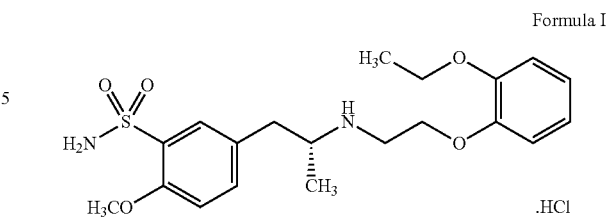

Formula I which comprises
(i) reacting (R)-(−)-5-(2-aminopropyl)-2-methoxybenzenesulfonamide of Formula II,

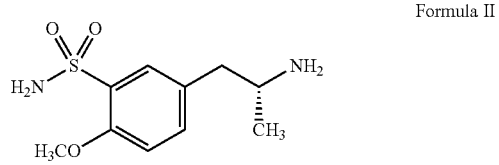

Formula II with substituted phenoxy compound of Formula III,

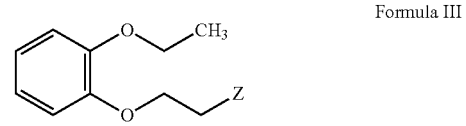

Formula III wherein Z represents a leaving group selected from —OSO$_2$CH$_3$, —SO$_2$C$_6$H$_4$CH$_3$, —F, —Br, —Cl, or —I, in a solvent in the presence of an alkaline earth metal oxide to obtain Tamsulosin base; and
(ii) converting Tamsulosin base into hydrochloride salt in a solvent by addition of aqueous hydrochloric acid.

2. The process according to claim 1, wherein the alkaline earth metal oxide is selected from calcium oxide, magnesium oxide and barium oxide.

3. The process according to claim 1, wherein the solvent used in step (i) is selected from methanol, ethanol, isopropanol, isobutyl alcohol and mixtures thereof.

4. The process according to claim 3, wherein the solvent is isobutyl alcohol.

5. The process according to claim 1, wherein the step (i) reaction is carried out at 80-90° C.

6. The process according to claim 1, wherein the solvent used in step (ii) is selected from methanol, ethanol, isopropanol, isobutyl alcohol and mixtures thereof.

7. The process according to claim 1, wherein Tamsulosin hydrochloride is further purified by dissolving in a solvent selected from methanol, ethanol, isopropanol, isobutyl alcohol and mixtures thereof, and precipitating the pure Tamsulosin hydrochloride.

* * * * *